US008295940B2

(12) United States Patent
Sherman

(10) Patent No.: US 8,295,940 B2
(45) Date of Patent: Oct. 23, 2012

(54) SYSTEM FOR RECHARGING MEDICAL INSTRUMENTS

(75) Inventor: Jason T. Sherman, Warsaw, IN (US)

(73) Assignee: De Puy Products, Inc., Warsaw, IN (US)

( * ) Notice: Subject to any disclaimer, the term of this patent is extended or adjusted under 35 U.S.C. 154(b) by 1622 days.

(21) Appl. No.: 11/016,290

(22) Filed: Dec. 17, 2004

(65) Prior Publication Data

US 2006/0131193 A1    Jun. 22, 2006

(51) Int. Cl.
 *A61N 1/378* (2006.01)
(52) U.S. Cl. .................. 607/61; 607/5; 607/35; 607/46; 607/60
(58) Field of Classification Search ................ 607/2, 46, 607/5, 61, 60, 35; 206/210, 363, 370
See application file for complete search history.

(56) References Cited

U.S. PATENT DOCUMENTS

| | | | | |
|---|---|---|---|---|
| 4,397,055 A | * | 8/1983 | Cuchiara | ........................ 15/22.1 |
| 6,096,264 A | * | 8/2000 | Peifer | ............................... 422/1 |
| 6,666,875 B1 | * | 12/2003 | Sakurai et al. | ................ 606/169 |
| 6,831,225 B2 | * | 12/2004 | Chandler | ........................ 174/50 |
| 6,960,988 B2 | * | 11/2005 | Blink et al. | .............. 340/286.09 |
| 2004/0116952 A1 | | 6/2004 | Sakurai et al. | |
| 2004/0129595 A1 | * | 7/2004 | Dane et al. | ..................... 206/503 |

OTHER PUBLICATIONS

European Search Report for European Patent Application No. 05257766.5, Mar. 15, 2010, 3 pgs.

* cited by examiner

*Primary Examiner* — Carl H Layno
*Assistant Examiner* — Natasha Patel
(74) *Attorney, Agent, or Firm* — Barnes & Thornburg LLP

(57) ABSTRACT

A system for recharging medical instruments comprises a medical instrument tray defining a plurality of recesses therein for receiving and storing a corresponding plurality of medical instruments. At least one of the medical instruments includes a secondary coil coupled to a rechargeable voltage source. The medical instrument tray includes a primary coil positioned at least partially about one or more of the recesses configured to receive and store one of the medical instruments. The primary coil couples to the secondary coil to charge the rechargeable voltage source when the corresponding medical instrument is received in the recess. A storage container is provided for receiving and storing one or more such medical instrument trays. The storage container includes an electrical routing system for routing voltage from an external voltage source to the primary coils.

24 Claims, 5 Drawing Sheets

SYSTEM FOR RECHARGING MEDICAL INSTRUMENTS

FIELD OF THE INVENTION

The present invention relates generally to systems for recharging rechargeable voltage sources, and more specifically to such systems for recharging medical instruments having rechargeable voltage sources.

BACKGROUND

During the lifetime of a patient, it may be desirable to perform one or more surgical procedures on the patent as a result of, for example, disease or trauma. Some such procedures involve the use of electrically operated instruments that may include rechargeable voltage sources.

SUMMARY

This disclosure is directed to a system for recharging rechargeable voltage sources of the type carried by medical instruments. The present invention may comprise one or more of the features recited in the attached claims, and/or one or more of the following features and combinations thereof. A system for recharging medical instruments may comprise a medical instrument tray defining a plurality of recesses therein for receiving and storing a corresponding plurality of medical instruments. At least one of the plurality of medical instruments may include a secondary coil coupled to a rechargeable voltage source. The medical instrument tray may include a primary coil positioned at least partially about one of the plurality of recesses configured to receive and store the at least one of the plurality of medical instruments. The primary coil may couple to the secondary coil to charge the rechargeable voltage source when the at least one of the plurality of medical instruments is received in the one of the plurality of recesses. A storage container may be provided for receiving and storing the medical instrument tray. The storage container may include an electrical routing system for routing voltage from an external voltage source to the primary coil.

The at least one of the plurality of medical instruments may have an upright position and a prostrate position, and the one of the plurality of recesses may be configured to receive and store the medical instrument in the upright position. Alternatively, the one of the plurality of recesses may be configured to receive and store the medical instrument in the prostrate position.

The medical instrument tray may comprise a bottom tray member defining the one of the plurality of recesses therein. A first coil member may extend at least partially about the one of the plurality of recesses. A top tray member may include a second coil member, and the top tray member may be configured to at least partially cover the bottom tray member so that the second coil member is electrically connected to the first coil member and so that the first and second coil members cooperate to form the primary coil. The secondary coil may be positioned relative to the at least one of the plurality of medical instruments so that the first coil member extends about a first portion of the secondary coil and the second coil member extends about a second portion of the secondary coil when the at least one of the plurality of medical instruments is received within the one of the plurality of recesses and the top tray member covers the bottom tray member.

Alternatively, the primary coil may circumscribe at least a portion of the one of the plurality of recesses with the one of the plurality of recesses configured so that the primary coil circumscribes the secondary coil when the at least one of the plurality of medical instruments is received within the one of the plurality of recesses.

The external voltage source may be an AC voltage source. The at least one of the plurality of medical instruments may include an AC-to-DC conversion circuit interposed between the secondary coil and the rechargeable voltage source, the AC-to-DC conversion circuit converting AC voltage induced in the secondary coil by the primary coil to a DC voltage, the DC voltage recharging the rechargeable voltage source. The at least one of the plurality of medical instruments may include a charge activation circuit having a switch positioned between the AC-to-DC conversion circuit and the rechargeable voltage source, and a comparator circuit. The comparator circuit may be responsive to an output voltage of the rechargeable voltage source to control the switch to connect the AC-to-DC conversion circuit to the rechargeable voltage source when the output voltage of the rechargeable voltage source is below a reference voltage. The comparator circuit may be responsive to the output voltage of the rechargeable voltage source to control the switch to disconnect the AC-to-DC conversion circuit from the rechargeable voltage source when the output voltage of the rechargeable voltage source is above the reference voltage. The system may further include a visual indication device providing a visual indication of the operational state of the switch. The at least one of the plurality of medical instruments may include a visual indication device providing a visual indication distinguishing a recharging state of the rechargeable voltage source from a non-recharging state of the rechargeable voltage source.

A system for recharging medical instruments may comprise a plurality of medical instrument trays, each defining at least one recess for receiving and storing a medical instrument having a secondary coil coupled to a rechargeable voltage source. Each of the plurality of medical instrument trays may include a primary coil positioned at least partially about the at least one recess. The primary coil of each of the plurality of medical instrument trays may couple to the secondary coil of a corresponding one of the medical instruments to charge the rechargeable voltage source when the corresponding one of the medical instruments is received in the at least one recess. A storage container may be provided for receiving and storing the plurality of medical instrument trays. An electrical routing system may be provided for routing voltage from an external voltage source to the primary coil of each of the plurality of medical instrument trays.

The storage container may be configured to receive and store the plurality of medical instrument trays therein with the plurality of medical instrument trays stacked one atop another.

The electrical routing system may include at least one electrical connector mounted to each of the plurality of medical instrument trays and electrically connected to the corresponding primary coils. The at least one electrical connector may be mounted to each of the plurality of medical instrument trays configured to electrically connect to at least one corresponding electrical connector mounted to a supporting medical instrument tray and to electrically connect to at least a corresponding electrical connector mounted to a medical instrument tray supported thereby. The storage container may include a closable lid. The electrical routing system may further include an interlock allowing the electrical routing system to route voltage from the external voltage source to the primary coil of each of the plurality of medical instrument trays only when the closable lid is closed.

Alternatively the electrical routing system may include a pair of electrically conductive posts mounted within the storage container, and a corresponding pair of electrically conductive channels defined through each of the plurality of medical instrument trays and electrically connected to the corresponding primary coils. The electrical routing system may route voltage from the external voltage source to the primary coil of any one of the plurality of medical instrument trays when the pair of electrically conductive posts are received within the electrically conductive channels of the any one of the plurality of medical instrument trays.

These and other features of the present invention will become more apparent from the following description of the illustrative embodiments.

DESCRIPTION OF THE ILLUSTRATIVE EMBODIMENTS

Figure 1:
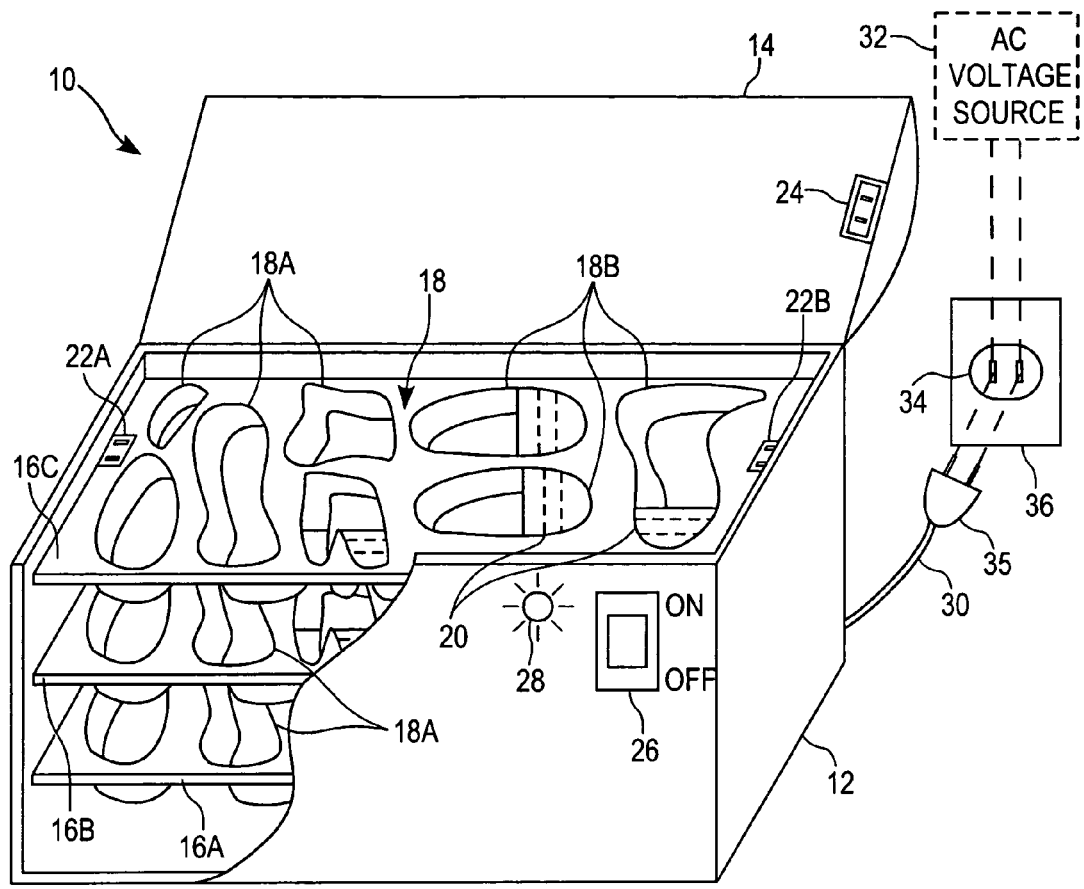
FIG. 1 is a front perspective view of a system for recharging medical instruments.

For the purposes of promoting an understanding of the principles of the invention, reference will now be made to a number of illustrative embodiments shown in the drawings and specific language will be used to describe the same.

Referring now to FIG. 1, a front perspective view of one illustrative system 10 for recharging medical instruments is shown. In the illustrated embodiment, the system 10 includes a five-sided medical instrument tray storage container 12 having a closable lid 14. The storage container 12 is shown in partial cutaway to illustrate three medical instrument trays 16A-16C stored therein in a stacked relationship with one tray atop another. It will be understood that while only three such trays 16A-16C are illustrated in FIG. 1, the medical instrument tray storage container 12 may alternatively be configured to hold more or fewer such trays. Additionally, while the three medical instrument storage trays 16A-16C are illustrated in FIG. 1 as being identical to each other, it will be understood any one or more of the trays 16A-16C may alternatively be configured to receive and store more or fewer identically, similarly or differently shaped medical instruments.

Each of the trays 16A-16C defines one or more recesses or receptacles, generally designated 18, that are configured to receive and store therein a correspondingly shaped medical instrument. Any of the trays 16A-16C may include one or more recesses or receptacles 18A that are configured to receive and store medical instruments that do not have one or more rechargeable voltage sources, and/or may include one or more recesses or receptacles 18B that are configured to receive and store rechargeable medical instruments. Each of the recesses or receptacles 18B includes structure, generally designated 20, for recharging a rechargeable voltage source carried by a medical instrument to be received and stored therein. It will be appreciated that any one or more of the medical instrument storage recesses or receptacles 18A and 18B may be configured to receive and store the corresponding medical instrument in a prostrate (e.g., prone, supine or on its side) position, or alternatively in a standing, upright position.

The system 10 includes an electrical routing system for routing voltage produced by an external voltage source 32 to the one or more recesses or receptacles 18B of each medical instrument storage tray 16A-16C. In the embodiment illustrated in FIG. 1, a portion of this electrical routing system includes a pair of electrical connectors 22A and 22B mounted to each tray 16A-16C along opposite edges thereof.

Figure 2:
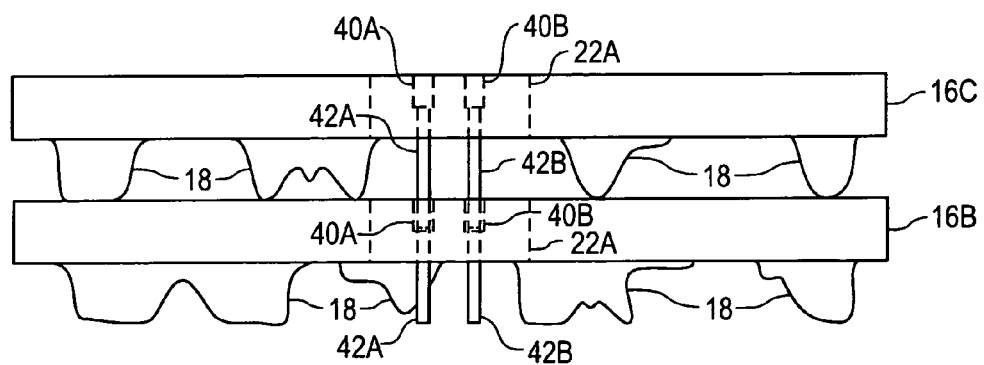
FIG. 2 is a side elevational view of two medical instrument trays stacked one atop the other and illustrating a portion of one embodiment of an electrical routing system for routing voltage from an external voltage source to the number of medical instrument trays carried by the instrument storage container as illustrated in FIG. 1.

Referring now to FIG. 2, a side elevational view of two such trays 16B and 16C are shown illustrating further details of one the electrical connectors 22A. The electrical connector 22A defines a pair of electrically conductive bores 40A and 40B extending into the connector 22A adjacent to the top surface of the medical instrument storage try 16B, 16C. A first electrical conductor 42A is electrically connected to the electrically conductive bore 40A, and extends downwardly from the electrical connector 22A and away from the bottom surface of the medical instrument storage tray 16B, 16C. Likewise, a second electrical conductor 42B is electrically connected to the electrically conductive bore 40B, and extends downwardly from the electrical connector 22A and away from the bottom surface of the medical instrument storage tray 16B, 16C. The electrical conductors 42A and 42B are sized in length so that they may be received within the electrically conductive bores 40A and 40B of a supporting medical instrument tray, such as illustrated by the electrical connection between the medical instrument storage trays 16C and 16B of FIG. 2. In this manner, any number of medical instrument storage trays may be electrically interconnected when stacked one upon another.

Referring again to FIG. 1, the medical instrument storage tray 16C is illustrated as including a pair of such electrical connectors 22A and 22B. In this illustrative embodiment, the electrical connectors 22A and 22B are positioned at identical locations relative to opposing side edges of the tray 16C and midway between the front and back edges so that the tray 16C so that the tray 16C may be received and stored within the storage container 12 with its front edge facing either the front or rear wall of the storage container 12 while still ensuring electrical contact to electrical medical storage trays above and below the tray 16C. It will be understood, however, that the present disclosure contemplates that each medical instrument storage tray 16A-16C may be configured to be received and stored within the medical instrument storage container 12 with a single tray orientation, and in such embodiments each tray 16A-16C need only have one of the electrical connectors 22A and 22B mounted thereto. The placement of such an electrical connector 22A or 22B relative to the tray in such cases may be arbitrary, and will typically be dictated by the specific application.

Figure 3:
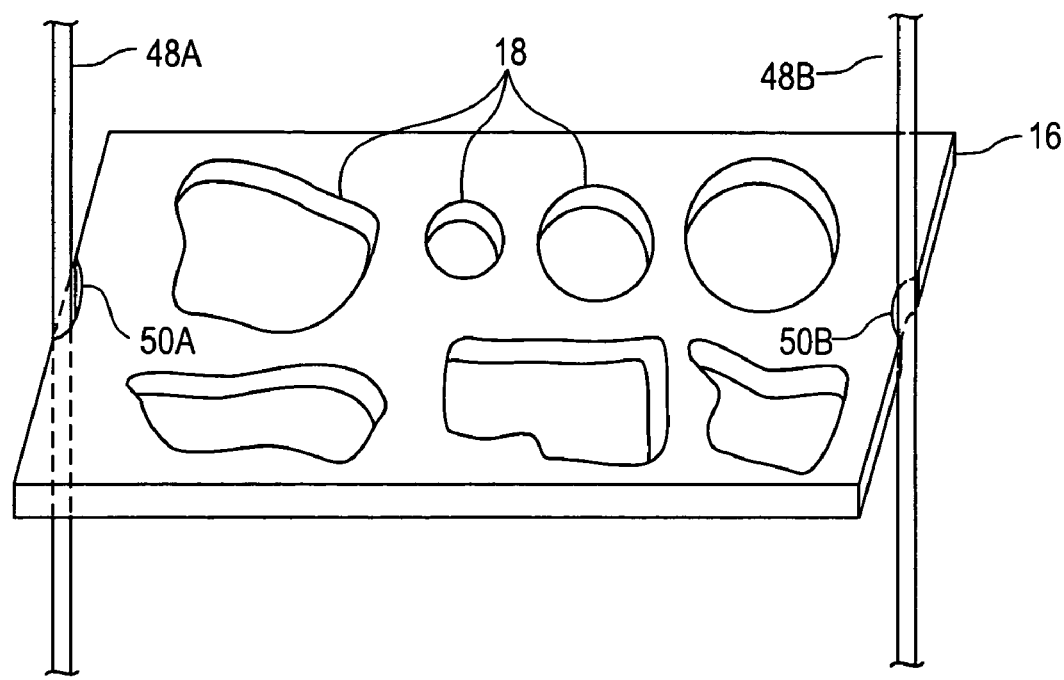
FIG. 3 is a perspective view of a portion of another embodiment of an electrical routing system for routing voltage from an external voltage source to the number of medical instrument trays carried by the instrument storage container as illustrated in FIG. 1.

Referring now to FIG. 3, an alternate embodiment of a portion of the electrical routing system for routing voltage from the external voltage source 32 to each medical instrument storage tray 16A-16C, is shown. In the embodiment illustrated in FIG. 3, the storage container 12 has a pair of electrically conductive rods or posts 48A and 48B mounted thereto, wherein the electrically conductive rods or posts 48A and 48B are configured to be electrically connected to the external voltage source 32 via conventional means. In this embodiment, each medical instrument storage tray, designated in FIG. 3 generally as 16, defines a pair of electrically conductive channels 50A and 50B along opposing side edges thereof. The electrically conductive channels 50A and 50B are configured to slidably receive the electrically conductive rods or posts 48A and 48B respectively therein so that the electrically conductive rod or post 48A is in electrical contact with the electrically conductive channel 50A and the electrically conductive rod or post 48B is in electrical contact with the electrically conductive channel 50B. In this manner, multiple medical instruments storage trays 16 may be stacked one on top another and electrically interconnected via the electrically conductive rods or posts 48A and 48B and the correspondingly configured electrically conductive channels 50A and 50B.

Referring again to FIG. 1, the closable lid 14 of the medical instrument tray storage container 12 illustratively has another electrical connector 24 mounted thereto that is configured to electrically connect to the electrical connector 22B of the top-most medical instrument storage tray 16C when the lid 14 is closed. The electrical connector 24 is electrically connected through a switch 26 to an electrical connector 35 of an electrical cord 30. The electrical connector 35 is configured for electrical connection to an electrical connector 36 that is connected to, or forms part of, the external voltage source 32. In the illustrated embodiment, the external voltage source 32 is an AC voltage source, which may be any conventional AC voltage source such as a conventional electrical panel that is electrically connected to a conventional outlet box 36 having a conventional electrical receptacle 34 configured to receive a conventional electrical connector 35 mounted to the terminal end of the electrical cord 30. It will be understood, however, that the external voltage source 32 may be provided in the form of other conventional voltage sources 32 with suitable electrical connections to the electrical cord 30. In any case, voltage from the external voltage source 32 is supplied to each of the medical instrument storage trays 16A-16C in the embodiment illustrated in FIG. 1 only if the lid 14 is in the closed position so that the electrical connector 24 comes into electrical contact with the electrical connector 22B, the electrical connector 35 is electrically connected to the external voltage source 32, and the switch 26 is in the "on" position.

This arrangement provides for a safety feature in that the medical instrument storage tray 16A-16C cannot be electrically energized unless and until the lid 14 is closed, the electrical cord 30 is connected to the external voltage source 32 and the switch 26 is in its "on" position. In an alternative embodiment, the electrical routing system may be provided with a safety interlock mechanism positioned between the lid 14 and the storage container 12 that allows the electrical routing system to route voltage from the external voltage source 32 to the primary coil of each of the plurality of medical instrument trays 16A-16C only when the closable lid 14 is closed. The safety interlock mechanism may be provided in the form of, for example, a reed switch, an optical switch or the like that allows the power switch 26 to be operated only when the lid 14 is closed. Optionally, such a safety interlock mechanism may also be configured to disallow opening of the lid 14 as long as the power switch 26 is in the "on" position. In this embodiment, the electrical connector 24 may be omitted, and a safety interlock mechanism of the type just described may instead be implemented. In any case, such elaborate safety measures are not strictly required by the system 10, however, and other conventional electrical connection systems for routing voltage from the electrical cord 30 to the medical instrument storage trays 16A-16C are contemplated. The storage container 12 further includes a visual indicator device 28, e.g., LED, lamp or the like, that is energized or activated when the electrical cord 30 is electrically connected to the external voltage source 32 and the switch 26 is in the "on" position. Activation of the visual indicator device 28 thus provides a visual indication of when voltage from the external voltage source 32 is being provided to the medical instrument storage trays 16A-16C.

Figure 4:
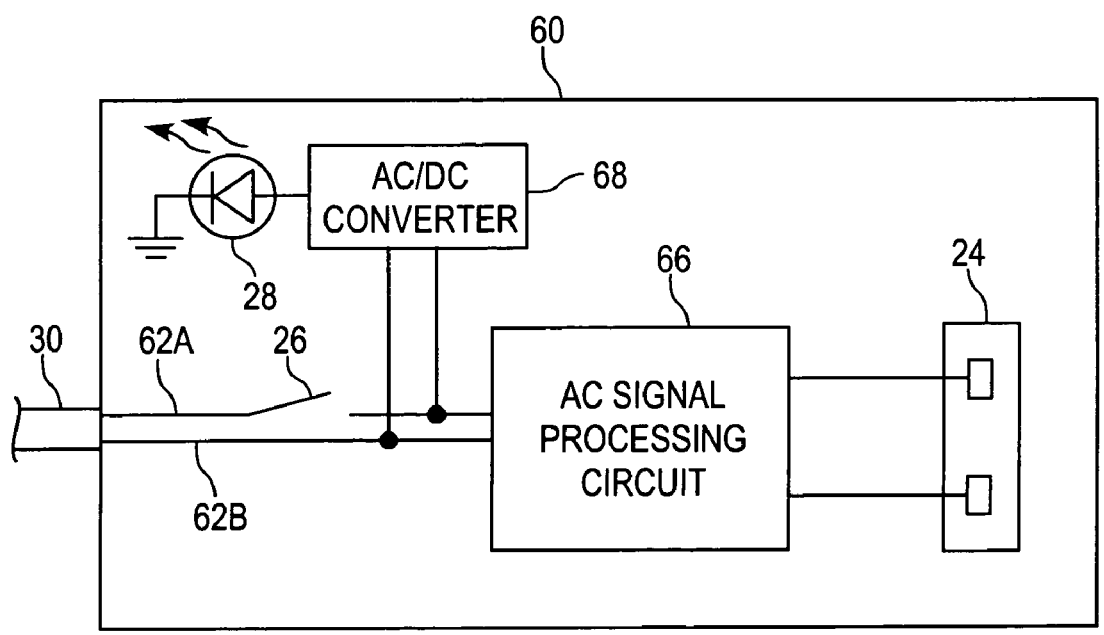
FIG. 4 is a schematic diagram illustrating one embodiment of a signal processing circuit for processing voltage from an external voltage source prior to routing the processed voltage to the number of medical instrument trays.

Referring now to FIG. 4, a schematic diagram is shown of one illustrative embodiment of a signal conditioning circuit 60 for conditioning the voltage supplied by the external voltage source 32 and routing this conditioned voltage to the number of medical instrument storage trays 16 as illustrated and described herein. Although not specifically illustrated in FIG. 1, the signal conditioning circuit 60 may mounted to, on or within the medical instrument storage container 12, and is interposed between the electrical cord 30 and the electrical connector 24 shown in FIG. 1. Alternatively, the signal conditioning circuit 60 may be a wall-mounted brick transformer mounted to a wall of the storage container 12, to the wall supporting the electrical receptacle 34 or to some other wall remote to the storage container 12. In the embodiment illustrated in FIG. 4, the electrical cord 30 includes a first electrical conductor 62A that is electrically connected through the switch 26 to one input of a signal processing circuit 66 having a second input electrically connected to a second electrical conductor 62B forming part of the electrical cord 30. The inputs of the signal processing circuit 66 are also electrically connected to a conventional AC-to-DC converter circuit 68 configured to convert AC voltage to a suitable DC voltage. An output of the converter circuit 68 is connected to the visual indicator device 28. The visual indicator device 28 is energized or activated whenever the electrical cord 30 is electrically connected to the external voltage source 32 and the switch 26 is closed or in the "on" position and the lid 14 is closed.

Signal outputs of the signal processing circuit 66 are electrically connected to the electrical connector 24 as shown. The signal processing circuit 66 is configured to condition the voltage produced by the external voltage source 32 in a conventional manner and provide a processed output voltage that is optimized, or at least suitable, for inducing a voltage in one conventional inductor or coil from another. In one embodiment, for example, the external voltage source 32 is a conventional 120 volt, 60 Hz signal, and the signal processing circuit 66 is configured in a conventional manner to clamp the signal amplitude to a reduced amplitude value and to increase or decrease the frequency to a frequency optimized or suitable for inducing voltage in one inductive coil by another. Those skilled in the art will recognize that the signal processing circuit 66 may alternatively be configured to process voltages produced by other external voltage sources 32 to achieve these results.

It will be appreciated that while a number of embodiments of an electrical routing system for routing voltage from the external voltage source 32 to the one or more medical instruments storage trays 16A-16C have been illustrated and described herein, such illustrative embodiment are provided by way of example. The present disclosure contemplates other conventional electrical routing systems for effectuating this transfer of voltage from the external voltage source 32 to the medical instrument storage trays 16A-16C, and the electrical routing system embodiments illustrated and described herein are accordingly not intended to be limiting in any way. Similarly, while only a single embodiment of a medical instrument tray storage container 12 has been illustrated and described herein, the present disclosure contemplates other embodiments and configurations of the container 12, and the illustrated container 12 is accordingly not intended to be limiting in any way.

Figure 5A:
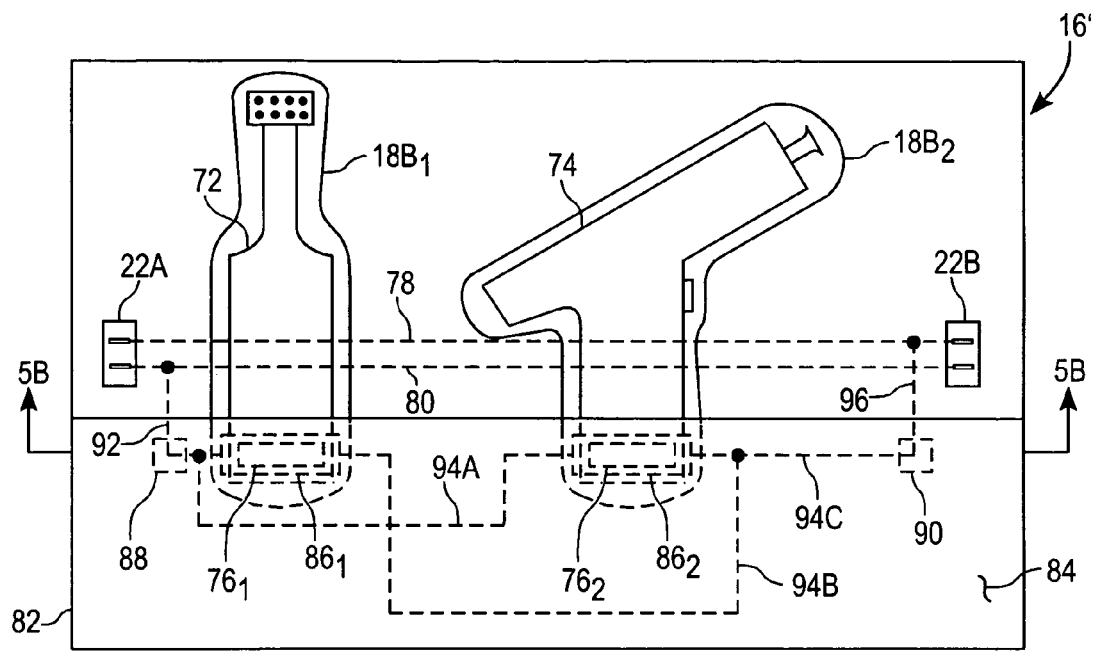
FIG. 5A is a top plan view of one embodiment of a medical instrument tray configured for recharging rechargeable voltage sources associated with one or more medical instruments.
Figure 5B:
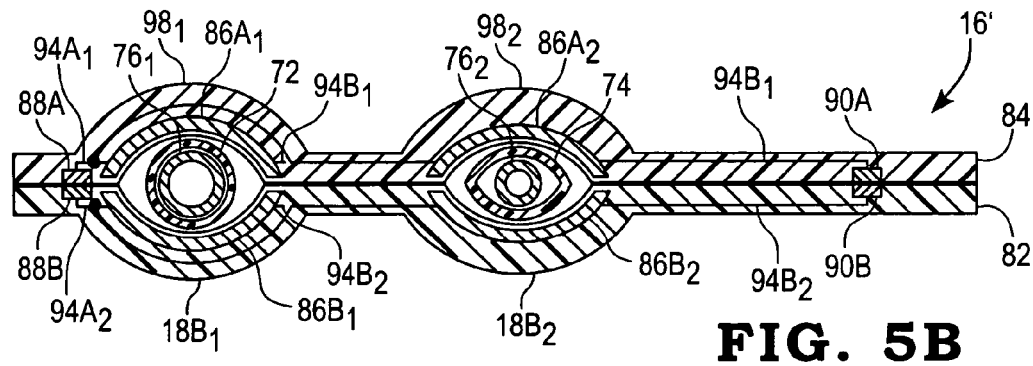
FIG. 5B is a cross-sectional view, taken along section lines 5B-5B of FIG. 5A, illustrating details relating to the structure of, and electrical interconnections to, the primary coils carried by the medical instrument tray of FIG. 5A.
Figure 5C:
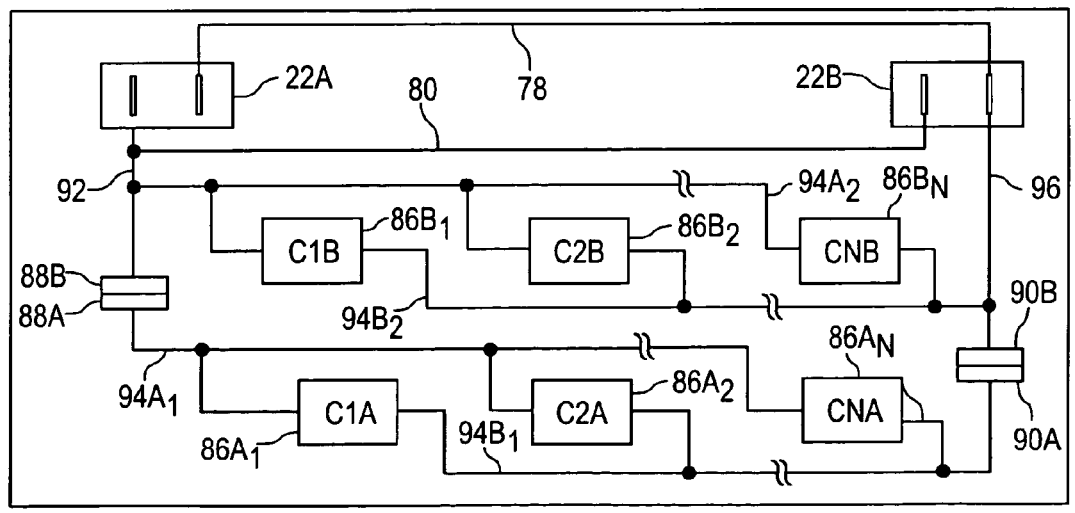
FIG. 5C is a schematic diagram illustrating a portion of one embodiment of an electrical routing system for routing a charging voltage to any number of primary coils of the type carried by the medical instrument tray of FIGS. 5A and 5B.

Referring now to FIGS. 5A-5C, one illustrative embodiment of a medical instrument storage tray 16' is shown which may be implemented as any one or more of the medical instrument storage trays 16A-16C shown in FIG. 1. For ease of illustration, the tray 16' is illustrated as having electrical connectors 22A and 22B mounted thereto as described hereinabove, although it will be understood that the tray 16' may alternatively be configured for electrical connection to the external voltage source 32 in any conventional manner as described hereinabove. Referring specifically to FIG. 5A, the medical instrument storage tray 16' includes a bottom tray member 82 and a top tray member 84, wherein the bottom tray member 82 defines at least two recesses or receptacles $18B_1$ and $18B_2$ therein. The recesses or receptacles $18B_1$ and $18B_2$ are sized to receive and store therein correspondingly shaped medical instruments 72 and 74, wherein the medical instruments 72 and 74 each include a rechargeable voltage source electrically coupled to a conventional inductive secondary coil $76_1$ and $76_2$ respectively. It will be understood that the bottom tray member 82 may define more or fewer such recesses or receptacles, and may additionally define one or more recesses or receptacles sized and configured to receive and store medical instruments that do not include rechargeable voltage sources. The two recesses or receptacles $18B_1$ and $18B_2$ are thus illustrated in FIGS. 5A and 5B only by way of example, and should not limit in any way the medical instrument storage configuration and capacity of the storage tray 16'.

One conductor of the electrical connector 22A is electrically connected to a corresponding conductor of the electrical connector 22B via a signal path 78, and the remaining conductor of the electrical connector 22A is likewise electrically connected to the remaining conductor of the electrical connector 22B via another signal path 80. The signal path 80 is also electrically connected to an electrical contact point 88, established between the top and bottom tray members 82 and 84 respectively, via a signal path 92. In the illustrated embodiment, the electrical contact point 88 includes separate electrical contact members 88A and 88B carried by each of the top and bottom tray members 82 and 84 respectively, as most clearly shown in FIG. 5B, wherein the electrical contact members 88A and 88B are conventional metallic electrical contacts that come into physical and electrical contact when the top tray member 84 is secured to the bottom tray member 82. It will be understood, however, that that the electrical contact members 88A and 88B may alternatively be provided in the form of two or more conventional electrical connectors configured to make electrical contact with each other when the top tray member 84 is secured to the bottom tray member 82.

Referring again to FIG. 5A, the electrical contact point 88 is electrically connected to one end of a signal path 94A having an opposite end electrically connected to an input of an inductive primary coil $86_1$ carried by the medical instrument storage tray 16' such that the primary coil $86_1$ is juxtaposed with, and extends at least partially about, the secondary coil $76_1$ contained within the medical instrument 72. The opposite end of the signal path 94A is also electrically connected to an input of another inductive primary coil $86_2$ carried by the medical instrument storage tray 16' such that the primary coil $86_2$ is juxtaposed with, and extends at least partially about, the secondary coil $76_2$ contained within the medical instrument 74. The outputs of the primary coils $86_1$ and $86_2$ are electrically connected to another electrical contact point 90, established between the top and bottom tray members 82 and 84 respectively, via a signal path 94B. The electrical contact point 90 is electrically connected to the signal path 78 via a signal path 96. In the illustrated embodiment, the electrical contact point 90 includes separate electrical contact members 90A and 90B carried by each of the top and bottom tray members 82 and 84 respectively, as most clearly shown in FIG. 5B, wherein the electrical contact members 90A and 90B are conventional metallic electrical contacts that come into physical and electrical contact when the top tray member 84 is secured to the bottom tray member 82. It will be understood, however, that that the electrical contact members 90A and 90B may alternatively be provided in the form of two or more conventional electrical connectors configured to make electrical contact with each other when the top tray member 84 is secured to the bottom tray member 82.

Referring now to FIG. 5B, a cross-sectional view of the medical instrument storage tray 16' of FIG. 5A, taken along sectional lines 5B-5B, is shown. In the illustrated embodiment, the top tray member 84 defines a recessed portion $98_1$ that is positioned over the recess $18B_1$ defined in the bottom tray member 82, and another recessed portion $98_2$ positioned over the recess $18B_2$ defined in the bottom tray member 82. In this embodiment, the primary coils $86_1$ and $86_2$ are each divided into two separate coil members with one coil member associated with the bottom tray member 82 and the other coil member associated with the top tray member 84. For example, the primary coil $86_1$ includes a semi-annular top coil member $86A_1$ extending at least partially about a top recess or receptacle $98_1$ defined by the top tray member 84, wherein the top coil member $86A_1$ is positioned relative to the top recess or receptacle $98_1$ to be juxtaposed over, and extend slightly less than 180 degrees about, the secondary coil $76_1$ contained within the medical instrument 72. The primary coil $86_1$ further includes a semi-annular bottom coil member $86B_1$ extending at least partially about the recess or receptacle $18B_1$ defined by the bottom tray member 82, wherein the bottom coil member $86B_1$ is positioned relative to the recess or receptacle $18B_1$ to be juxtaposed under, and extending slightly less than 180 degrees about, the secondary coil $76_1$ contained within the medical instrument 72. Together, the top and bottom coil members $86A_1$ and $86B_1$ are positioned relative to the corresponding top and bottom recesses or receptacles $98_1$ and $18B_1$ to be adjacent to, and extend slightly less than 360 degrees about, the secondary coil $76_1$ of the medical instrument 72 when the medical instrument 72 is received within the recess or receptacle $18B_1$. Likewise, the primary coil $86_2$ includes top and bottom semi-annular coil members $86A_2$ and $86B_2$ positioned relative to corresponding top and bottom recesses or receptacles $98_2$ and $18B_2$ to be adjacent to, and extend slightly less than 360 degrees about, the secondary coil $76_2$ contained within the medical instrument 74 when the medical instrument 74 is received within the recess or receptacle $18B_2$.

In the embodiment illustrated in FIG. 5B, the coil members $86A_1$, $86B_1$, $86A_2$ and $86B_2$ are shown embedded within the respective top and bottom tray members 84 and 82. In this embodiment, the top and bottom tray members 84 and 82 are formed of a moldable, electrically insulating material, e.g., a plastic resin, and the coil members $86A_1$, $86B_1$, $86A_2$ and $86B_2$ may be embedded within the respective top and bottom tray members 84 and 82 via conventional molding technology. Alternatively, the coil members $86A_1$, $86B_1$, $86A_2$ and $86B_2$ may be mounted to the respective top and bottom tray members 84 and 82. In either case, it is desirable to minimize the distances between open ends of the opposite coil member pairs $86A_1$, $86B_1$ and $86A_2$, $86B_2$ to thereby maximize or optimize the energy transfer efficiency between the primary/secondary coil pairs $86_1$, $76_1$ and $86_2$, $76_2$. It will further be appreciated that the coil members $86A_1$, $86B_1$, $86A_2$ and $86B_2$ need not be semi-annular as illustrated in FIG. 5B, but may instead take on any desired shape that each extend at least partially about the periphery of the corresponding recess or receptacle $98_1$, $18B_1$, $98_2$ and $18B_2$ respectively as described hereinabove.

In the embodiment illustrated in FIG. 5A, the top tray member 84 is sized to cover only a portion of the recesses or receptacles $18B_1$ and $18B_2$. Alternatively, the top tray member 84 may be sized to cover more, or different portions of, the bottom tray member 82, as long as the top tray member 84 covers appropriate portions of the recesses or receptacles $18B_1$, $18B_2$ so that the primary coils $86_1$, $86_2$ carried by the top tray member 84 are juxtaposed with the secondary coils $76_1$, $76_2$ of the instruments 72, 74 respectively when the instruments 72 and 74 are stored therein.

Referring now to FIG. 5C, a schematic diagram is shown illustrating a portion of one embodiment of an electrical routing system for routing the voltage produced by the external voltage source 32 and supplied to the medical instrument storage tray 16' to any number of primary coils of the type carried by the medical instrument tray 16' of FIGS. 5A and 5B. In the illustrated embodiment, one signal conductor of the electrical connector 22A is electrically connected via the signal path 78 to an identical signal conductor of the electrical connector 22B, and the opposite electrical conductor of the electrical connector 22A is connected via the signal path 80 to the corresponding opposite electrical conductor of the electrical connector 22B. The signal path 92 connects the signal path 80 to the electrical contact 88B carried by the bottom tray member 82, and also connects to a signal path $94A_2$ that is connected to the inputs of any number, N, of primary coil members C1B, C2B, ..., CNB carried by the bottom tray member 82, wherein N may be any positive integer. A signal path $94B_2$ electrically connects the outputs of the N primary coil members C1B, C2B, ..., CNB to the electrical contact 90B carried by the bottom tray member 82 and also to the signal path 96 that is electrically connected to the signal path 78. The electrical contact 88A carried by the top tray member 84 electrically contacts the electrical contact 88B when the top tray member 84 is secured to the bottom tray member 82, and the electrical contact 88A is electrically connected to a signal path $94A_1$ that is connected to the inputs of any corresponding number, N, of primary coil members C1A, C2A, ..., CNA carried by the top tray member 84. A signal path $94B_1$ electrically connects the outputs of the N primary coil members C1A, C2A, ..., CNA to the electrical contact 90A carried by the top tray member 84 that electrically contacts the electrical contact 90B when the top tray member 84 is secured to the bottom tray member 82.

Figure 6A:
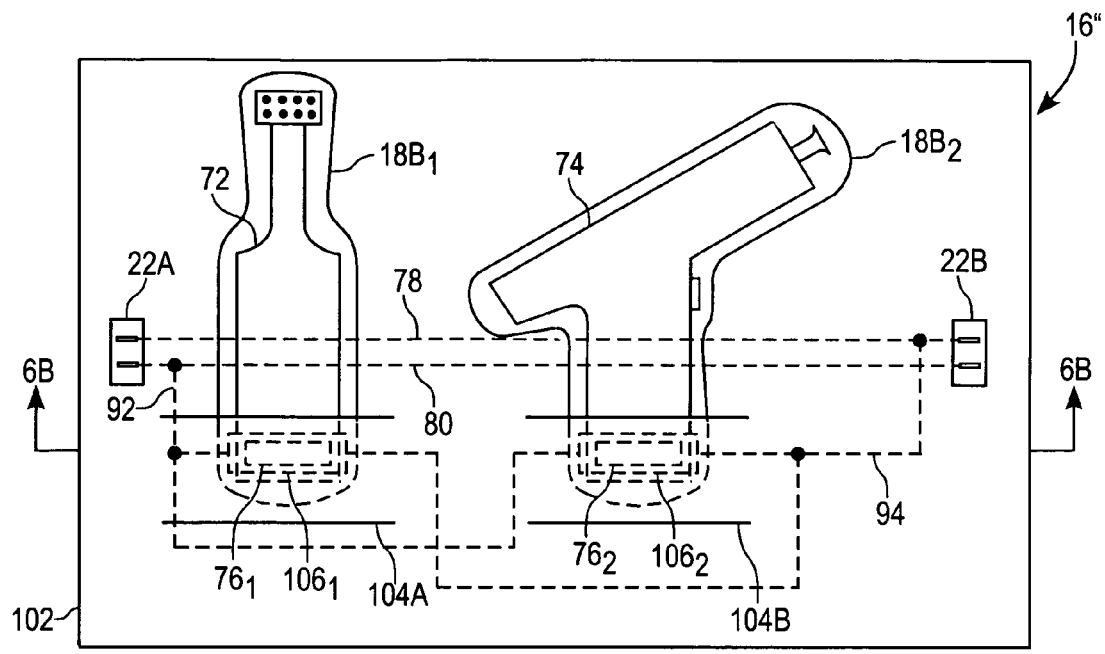
FIG. 6A is a top plan view of another embodiment of a medical instrument tray configured for recharging rechargeable voltage sources associated with one or more medical instruments.
Figure 6B:
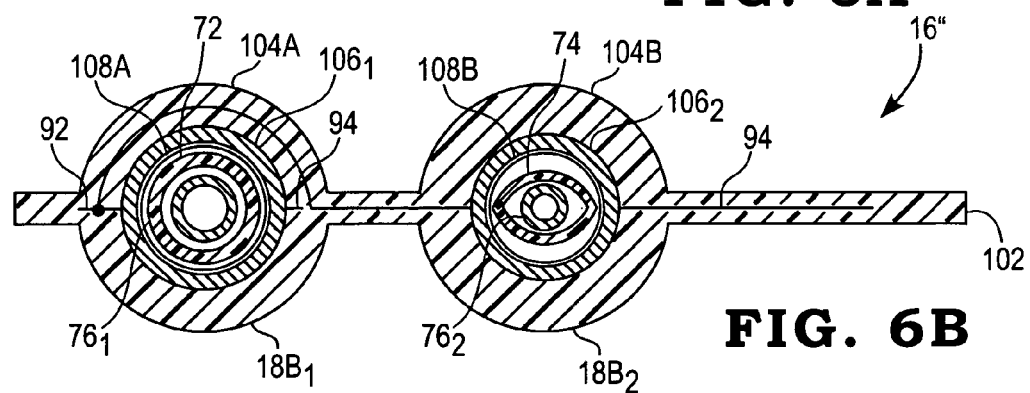
FIG. 6B is a cross-sectional view, taken along section lines 6B-6B of FIG. 6A, illustrating details relating to the structure of, and electrical interconnections to, the primary coils carried by the medical instrument tray of FIG. 6A.
Figure 6C:
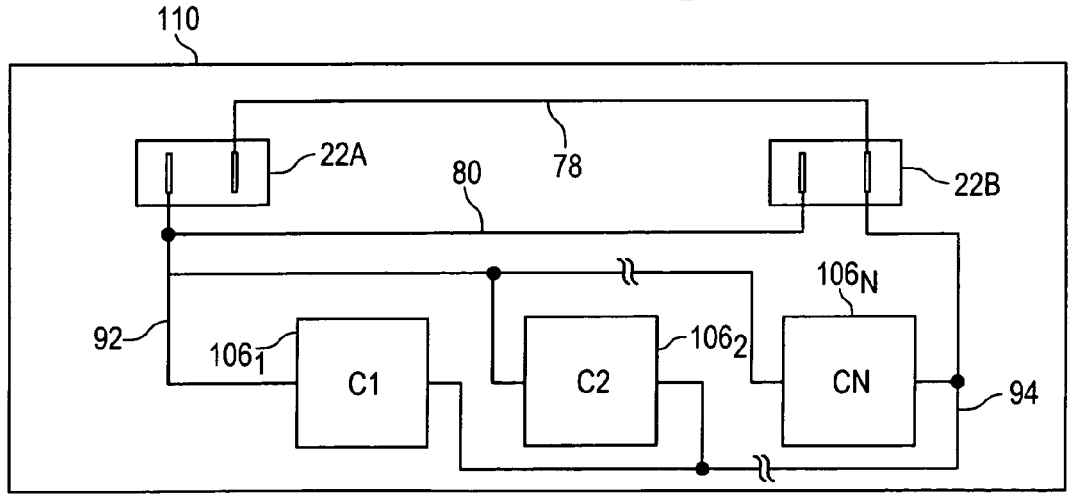
FIG. 6C is a schematic diagram illustrating a portion of one embodiment of an electrical routing system for routing a charging voltage to any number of primary coils of the type carried by the medical instrument tray of FIGS. 6A and 6B.

Referring now to FIGS. 6A-6C, another illustrative embodiment of a medical instrument storage tray 16" is shown which may be implemented as any one or more of the medical instrument storage trays 16A-16C shown in FIG. 1. For ease of illustration, the tray 16" is illustrated as having electrical connectors 22A and 22B mounted thereto as described hereinabove, although it will be understood that the tray 16" may alternatively be configured for electrical connection to the external voltage source 32 in any conventional manner as described hereinabove. Referring specifically to FIG. 6A, the medical instrument storage tray 16" includes a tray member 102 defining at least two recesses or receptacles $18B_1$ and $18B_2$ therein. The recesses or receptacles $18B_1$ and $18B_2$ are sized to receive and store therein correspondingly shaped medical instruments 72 and 74, wherein the medical instruments 72 and 74 each include a rechargeable voltage source electrically coupled to a conventional inductive secondary coil $76_1$ and $76_2$ respectively. It will be understood that the tray member 102 may define more or fewer such recesses or receptacles, and may additionally define one or more recesses or receptacles sized and configured to receive and store medical instruments that do not include rechargeable voltage sources. The two recesses or receptacles $18B_1$ and $18B_2$ are thus illustrated in FIGS. 6A and 6B only by way of example, and should not limit in any way the medical instrument storage configuration and capacity of the storage tray 16".

One conductor of the electrical connector 22A is electrically connected to a corresponding conductor of the electrical connector 22B via a signal path 78, and the remaining conductor of the electrical connector 22A is likewise electrically connected to the remaining conductor of the electrical connector 22B via another signal path 80. The signal path 80 is also electrically connected to a signal path 92 that is electrically connected to the input of an inductive primary coil $106_1$ carried by the medical instrument storage tray 16" such that the primary coil $106_1$ is juxtaposed with, and extends at least partially about, the secondary coil $76_1$ contained within the medical instrument 72. The signal path 92 is also electrically connected to an input of another inductive primary coil $106_2$ carried by the medical instrument storage tray 16" such that the primary coil $86_2$ is juxtaposed with, and extends at least partially about, the secondary coil $76_2$ contained within the medical instrument 74. The outputs of the primary coils $106_1$ and $106_2$ are electrically connected to the signal path 78 via a signal path 94.

Referring now to FIG. 6B, a cross-sectional view of the medical instrument storage tray 16" of FIG. 6A, taken along sectional lines 6B-6B, is shown. In the illustrated embodiment, the tray member 106 defines a recessed portion 104A that is positioned over the recess $18B_1$ defined in the tray member 102, and another recessed portion 104B positioned over the recess $18B_2$ defined in the tray member 102. In this embodiment, the tray member defines a first bore 108A between the recesses 104A and $18B_1$ and a second bore 108B between the recesses 104B and $18B_1$, wherein the bores 108A and 108B are sized to receive therein the portions of the medical instruments 72 and 74 respectively that contain the secondary coils $76_1$ and $76_2$ respectively. The primary coils $106_1$ and $106_2$ are each provided in the form of annular coils embedded within the tray member 102 and generally circumscribing the respective bores 108A and 108B. The primary coil $106_1$ thus extends entirely about the bore 108A defined by the recesses 104A and $18B_1$ so that the primary coil $106_1$ is positioned relative to the tray member 102 to be juxtaposed over, and extend completely about, the secondary coil $76_1$ contained within the medical instrument 72 when the medical instrument 72 is received within the recess 18B1. Likewise, the primary coil $106_2$ extends entirely about the bore 108B defined by the recesses 104B and $18B_2$ so that the primary coil $106_2$ is positioned relative to the tray member 102 to be juxtaposed over, and extend completely about, the secondary coil $76_2$ contained within the medical instrument 74 when the medical instrument 74 is received within the recess $18B_2$.

In the embodiment illustrated in FIG. 6B, the primary coils $106_1$ and $106_2$ are shown embedded within the tray member 102. In this embodiment, the tray member 102 is formed of a moldable, electrically insulating material, e.g., a plastic resin, and the primary coils $106_1$ and $106_2$ may be embedded within the tray member 102 via conventional molding technology. Alternatively, the primary coils $106_1$ and $106_2$ may be mounted to the tray member 102. It will be appreciated that the primary coils $106_1$ and $106_2$ need not be annular in shape as illustrated in FIG. 6B, but may instead take on any desired shape that extends entirely about the periphery of the corresponding recess or receptacle $18B_1$ and $18B_2$ respectively as described hereinabove.

Referring now to FIG. 6C, a schematic diagram is shown illustrating a portion of one embodiment of an electrical routing system for routing the voltage produced by the external voltage source 32 and supplied to the medical instrument storage tray 16" to any number of primary coils of the type carried by the medical instrument tray 16" of FIGS. 6A and 6B. In the illustrated embodiment, one signal conductor of the electrical connector 22A is electrically connected via the signal path 78 to an identical signal conductor of the electrical connector 22B, and the opposite electrical conductor of the electrical connector 22A is connected via the signal path 80 to the corresponding opposite electrical conductor of the electrical connector 22B. The signal path 92 connects the signal path 80 to the inputs of any number, N, of primary coils C1, C2, ..., CN carried by the tray member 102, wherein N may be any positive integer. The signal path 94 electrically connects the outputs of the N primary coils C1, C2, ..., CN to the signal path 78.

Figure 7:
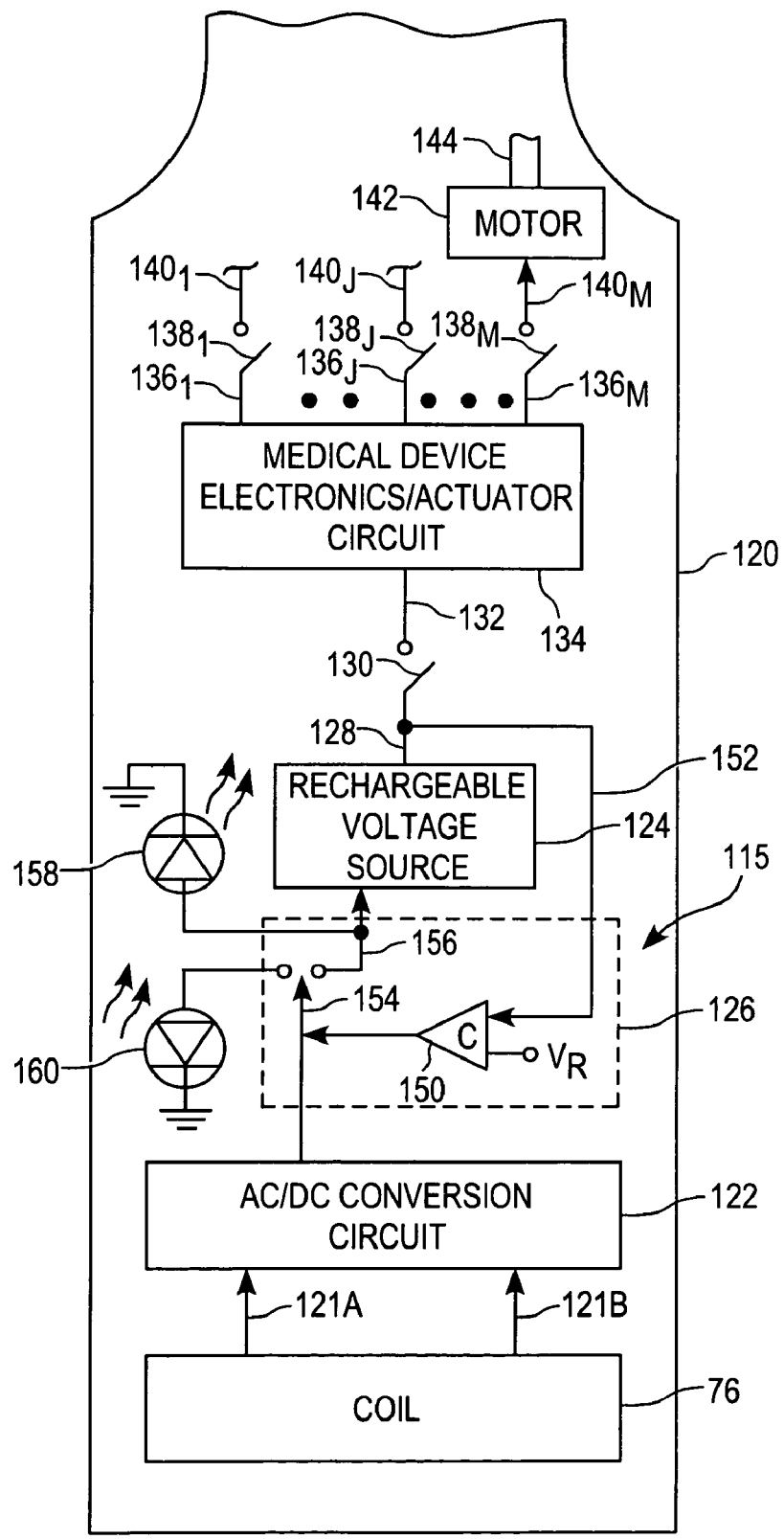
FIG. 7 is a schematic diagram illustrating one embodiment of a charging circuit carried by any of the rechargeable medical instruments illustrated herein.

Referring now to FIG. 7, a schematic diagram is shown illustrating one embodiment of a charging circuit 115 carried by a rechargeable medical instrument 120 wherein the instrument 120 is representative of any of the medical instruments shown and described herein that include a rechargeable voltage source. In the illustrated embodiment, the charging circuit 115 includes a secondary coil, generally designated 76, that is electrically connected to an AC-to-DC conversion circuit 122 via signal paths 121A and 121B. A DC output signal path of the AC-to-DC conversion circuit 122 is electrically connected to a switch 154 forming part of a charge activation circuit 126. An output 156 of the charge activation circuit 126 is electrically connected to a charging voltage input of a rechargeable voltage source 124 having a supply voltage output 128. The rechargeable voltage source 124 may be or include one or more conventional rechargeable batteries, conventional rechargeable capacitors or the like. In any case, the voltage output 128 of the rechargeable voltage source 124 is electrically connected to a voltage input 132 of a medical device electronics/actuator circuit 134 via a switch 130. The switch 130 will generally be a manually actuatable switch mounted to an external surface of the medical instrument 120, and may be manually actuated as desired to provide the supply voltage produced by the voltage source 124 to the circuit 134. The medical device electronics/actuator circuit 134 is electrically connected to a number, M, of medical device electronics/actuator circuit outputs $136_1$-$128_M$, wherein M may be any positive integer. The outputs $136_1$-$128_M$ are electrically connected to corresponding electronic feature and/or actuator inputs $140_1$-$140_M$ via a corresponding number of switches $138_1$-$138_M$. The switches $138_1$-$138_M$ will generally be manually actuatable switches mounted to an external surface of the medical instrument 120, and may be manually actuated as desired to activate operation of one or more corresponding functions of the medical instrument 120. For example, any number J of the signal paths $140_1$-$140_M$ may be used to provide operational information and/or other data to other electronic features associated with the medical instrument 120, wherein J may be any positive integer less than or equal to M. At least one of the signal paths $140_1$-$140_M$ may be connected to a motor 142 or other conventional drive mechanism to appropriately drive an output shaft 144 connected to a medical device implement such as a drill, saw or other actuatable mechanism.

The supply voltage output 128 of the rechargeable voltage source 124 is electrically connected to one input of a comparator circuit 150 forming part of the charge activation circuit 126. A second input of the comparator circuit 150 is electrically connected to a reference voltage $V_R$, which may be an independent voltage source or a fraction of the supply voltage produced by the rechargeable voltage source 124. In any case, an output of the comparator circuit 150 is electrically connected to the switch 154 so that operation of the comparator circuit 150 controls the position of the switch 154. The signal path 156, corresponding to one position of the switch 154, is electrically connected to a first visual indicator 158, e.g., LED, lamp or the like, and the opposite position of the switch 154 is electrically connected to another visual indicator device 160, e.g., LED, lamp or the like.

In operation, when the medical instrument 120 is received within a corresponding recess or receptacle 18B of the medical instrument storage tray; e.g., 16' or 16", with voltage from the external voltage source 32 supplied to a corresponding primary coil 86, 106 associated with the tray 16', 16", the primary coil 86, 106 will induce a corresponding voltage in the secondary coil 76 of the medical instrument 120 in a conventional manner. This induced voltage, which will generally be an AC voltage, is converted by the AC-to-DC conversion circuit 122 so that a corresponding DC voltage is supplied to the switch 154 of the charge activation circuit 126. If the operating voltage of the rechargeable voltage source 124 is greater than the reference voltage $V_R$, the output of the comparator circuit 150 will decouple the output of the AC-to-DC conversion circuit 122 from the rechargeable voltage source 124 and electrically connect the output of the AC-to-DC conversion circuit 122 to the visual indicator device 160. In this embodiment, the visual indicator device 160 thus acts as a "charging complete" indicator, and is activated by the charging circuit 115 whenever an appropriate AC voltage is induced in the coil 76 and the operating voltage of the rechargeable voltage source 124 is greater than the reference voltage, $V_R$. These conditions cause the switch 154 to disconnect the DC voltage produced by the AC-to-DC conversion circuit 122 from the charging input of the rechargeable voltage source 124 and instead route this voltage to the visual indicator device 160 to thereby indicate that the rechargeable voltage source 122 is fully charged. Disconnecting the AC-to-DC conversion circuit 122 from the rechargeable voltage source 124 when the rechargeable voltage source 124 is fully charged also provides a safety feature that avoids overcharging of the rechargeable voltage source 124. When no AC voltage is being induced in the secondary coil 76, no corresponding DC voltage will be produced by the AC-to-DC circuit 122 and the visual indicator 160 will accordingly be deactivated.

When the operating voltage of the rechargeable voltage source 124 drops below the reference voltage, $V_R$, the comparator circuit 150 controls the switch 154 to electrically connect the output of the AC-to-DC conversion circuit 122 to the charging voltage input of the rechargeable voltage source 124. With the medical instrument 120 received within a corresponding recess or receptacle 18B of the medical instrument storage tray 16', 16" so that the primary coil 86, 106 associated with the tray 16', 16" induces a corresponding voltage in the secondary coil 76, the corresponding DC voltage produced by the AC-to-DC conversion circuit 122 will be provided as a charging voltage to recharge the rechargeable voltage source 124. As this process is occurring, the DC voltage produced by the AC-to-DC conversion circuit 122 also activates the visual indicator device 158 to thereby provide a visual indication that the rechargeable voltage source 122 is being recharged.

While the invention has been illustrated and described in detail in the foregoing drawings and description, the same is to be considered as illustrative and not restrictive in character, it being understood that only illustrative embodiments thereof have been shown and described and that all changes and modifications that come within the spirit of the invention are desired to be protected. For example, while the primary coils $86_1$, $86_2$, $106_1$, $106_2$ are illustrated in FIGS. 5A-6C as being electrically connected in parallel, those skilled in the art will recognize that one or more of these primary coils may alternatively be electrically connected in series. In either case, techniques for compensating for phase relationships between any of the coil members and/or other optimization techniques would be within the knowledge of a skilled artisan.

What is claimed is:

1. A system for recharging medical instruments, the system comprising:
    a medical instrument tray defining a plurality of recesses therein for receiving and storing a corresponding plurality of medical instruments, at least one of the plurality of medical instruments including a secondary coil coupled to a rechargeable voltage source, the medical instrument tray including a primary coil positioned at least partially about one of the plurality of recesses configured to receive and store the at least one of the plurality of medical instruments, the primary coil coupling to the secondary coil to charge the rechargeable voltage source when the at least one of the plurality of medical instruments is received in the one of the plurality of recesses, and
    a storage container to removably receive and store the medical instrument tray, the storage container including an electrical routing system for routing voltage from an external voltage source to the primary coil.

2. The system of claim 1 wherein the at least one of the plurality of medical instruments has an upright position and a prostrate position,
    and wherein the one of the plurality of recesses is configured to receive and store the medical instrument in the upright position.

3. The system of claim 1 wherein the at least one of the plurality of medical instruments has an upright position and a prostrate position,
    and wherein the one of the plurality of recesses is configured to receive and store the medical instrument in the prostrate position.

4. The system of claim 1 wherein the medical instrument tray comprises:
    a bottom tray member defining the one of the plurality of recesses therein,
    a first coil member extending at least partially about the one of the plurality of recesses, and
    a top tray member including a second coil member, the top tray member configured to at least partially cover the bottom tray member so that the second coil member is electrically connected to the first coil member and so that the first and second coil members cooperate to form the primary coil.

5. The system of claim 4 wherein the secondary coil is positioned relative to the at least one of the plurality of medical instruments so that the first coil member extends about a first portion of the secondary coil and the second coil member extends about a second portion of the secondary coil when the at least one of the plurality of medical instruments is received within the one of the plurality of recesses and the top tray member covers the bottom tray member.

6. The system of claim 1 wherein the primary coil circumscribes at least a portion of the one of the plurality of recesses, the one of the plurality of recesses configured so that the primary coil circumscribes the secondary coil when the at least one of the plurality of medical instruments is received within the one of the plurality of recesses.

7. The system of claim 1 wherein the external voltage source is an AC voltage source.

8. The system of claim 7 wherein the at least one of the plurality of medical instruments includes an AC-to-DC conversion circuit interposed between the secondary coil and the rechargeable voltage source, the AC-to-DC conversion circuit converting AC voltage induced in the secondary coil by the first coil to a DC voltage, the DC voltage recharging the rechargeable voltage source.

9. The system of claim 8 wherein the at least one of the plurality of medical instruments includes a charge activation circuit having a switch positioned between the AC-to-DC conversion circuit and the rechargeable voltage source, and a comparator circuit, the comparator circuit responsive to an output voltage of the rechargeable voltage source to control the switch to connect the AC-to-DC conversion circuit to the rechargeable voltage source when the output voltage of the rechargeable voltage source is below a reference voltage, and to control the switch to disconnect the AC-to-DC conversion circuit from the rechargeable voltage source when the output voltage of the rechargeable voltage source is above the reference voltage.

10. The system of claim 9 further including a visual indication device providing a visual indication of the operational state of the switch.

11. The system of claim 1 wherein the at least one of the plurality of medical instruments includes a visual indication device providing a visual indication distinguishing a recharging state of the rechargeable voltage source from a non-recharging state of the rechargeable voltage source.

12. A system for recharging medical instruments, the system comprising:
    a plurality of medical instrument trays each defining at least one recess for receiving and storing a medical instrument having a secondary coil coupled to a rechargeable voltage source, each of the plurality of medical instrument trays including a primary coil positioned at least partially about the at least one recess, the primary coil of each of the plurality of medical instrument trays coupling to the secondary coil of a corresponding one of the medical instruments to charge the rechargeable voltage source when the corresponding one of the medical instruments is received in the at least one recess, a storage container to removably receive and store the plurality of medical instrument trays, and an electrical routing system for routing voltage from an external voltage source to the primary coil of each of the plurality of medical instrument trays.

13. The system of claim 12 wherein the medical instrument stored in any of the plurality of medical instrument trays has an upright position and a prostrate position, and wherein the at least one recess of any one or more of the plurality of medical instrument trays is configured to receive and store the corresponding medical instrument in the upright position.

14. The system of claim 12 wherein the medical instrument stored in any of the plurality of medical instrument trays has an upright position and a prostrate position, and wherein the at least one recess of any one or more of the plurality of medical instrument trays is configured to receive and store the corresponding medical instrument in the prostrate position.

15. The system of claim 12 wherein the storage container is configured to receive and store the plurality of medical instrument trays therein with the plurality of medical instrument trays stacked one atop another.

16. The system of claim 15 wherein the electrical routing system includes at least one electrical connector mounted to each of the plurality of medical instrument trays and electrically connected to the corresponding primary coils, the at least one electrical connector mounted to each of the plurality of medical instrument trays configured to electrically connect to at least one corresponding electrical connector mounted to a supporting medical instrument tray and to electrically connect to at least a corresponding electrical connector mounted to a medical instrument tray supported thereby.

17. The system of claim 16 wherein the storage container includes a closable lid, and wherein the electrical routing system further includes an interlock allowing the electrical routing system to route voltage from the external voltage source to the primary coil of each of the plurality of medical instrument trays only when the closable lid is closed.

18. The system of claim 15 wherein the electrical routing system includes:

a pair of electrically conductive posts mounted within the storage container, and a corresponding pair of electrically conductive channels defined through each of the plurality of medical instrument trays and electrically connected to the corresponding primary coils, the electrical routing system routing voltage from the external voltage source to the primary coil of any one of the plurality of medical instrument trays when the pair of electrically conductive posts are received within the electrically conductive channels of the any one of the plurality of medical instrument trays.

19. The system of claim 12 wherein the external voltage source is an AC voltage source.

20. The system of claim 19 wherein the electrical routing system includes an AC voltage processing circuit receiving an AC voltage from the AC voltage source and routing a resulting processed AC voltage to the primary coil of each of the plurality of medical instrument trays.

21. The system of claim 19 wherein the medical instrument includes an AC-to-DC conversion circuit interposed between the secondary coil and the rechargeable voltage source, the AC-to-DC conversion circuit converting AC voltage induced in the secondary coil by the primary coil to a DC voltage, the DC voltage recharging the rechargeable voltage source.

22. The system of claim 21 wherein the medical instrument includes a charge activation circuit having a switch positioned between the AC-to-DC conversion circuit and the rechargeable voltage source, and a comparator circuit, the comparator circuit responsive to an output voltage of the rechargeable voltage source to control the switch to connect the AC-to-DC conversion circuit to the rechargeable voltage source when the output voltage of the rechargeable voltage source is below a reference voltage, and to control the switch to disconnect the AC-to-DC conversion circuit from the rechargeable voltage source when the output voltage of the rechargeable voltage source is above the reference voltage.

23. The system of claim 22 further including a visual indication device providing a visual indication of the operational state of the switch.

24. The system of claim 12 wherein the medical instrument includes a visual indication device providing a visual indication distinguishing a recharging state of the rechargeable voltage source from a non-recharging state of the rechargeable voltage source.

* * * * *